(12) United States Patent
Brouillette

(10) Patent No.: US 7,320,677 B2
(45) Date of Patent: Jan. 22, 2008

(54) NEEDLELESS SYRINGE FOR THE DELIVERY OF THERAPEUTIC AGENTS

(75) Inventor: Martin Brouillette, Sherbrooke (CA)

(73) Assignee: Société de Commercialisation des Produits de la Recherche Appliquée - Socpra Sciences et Génie, S.E.C., Sherbrooke, Quebec (CA)

( * ) Notice: Subject to any disclaimer, the term of this patent is extended or adjusted under 35 U.S.C. 154(b) by 235 days.

(21) Appl. No.: 10/398,855

(22) PCT Filed: Oct. 19, 2001

(86) PCT No.: PCT/CA01/01491

§ 371 (c)(1),
(2), (4) Date: Aug. 15, 2003

(87) PCT Pub. No.: WO02/32483

PCT Pub. Date: Apr. 25, 2002

(65) Prior Publication Data

US 2004/0024350 A1   Feb. 5, 2004

(30) Foreign Application Priority Data

Oct. 20, 2000   (CA) .................................. 2324045

(51) Int. Cl.
*A61M 5/30* (2006.01)
(52) U.S. Cl. ........................................ 604/68; 604/69
(58) Field of Classification Search ............ 604/68–72, 604/48, 131, 140, 142, 147
See application file for complete search history.

(56) References Cited

U.S. PATENT DOCUMENTS

| 3,802,430 | A |   | 4/1974  | Schwebel et al. |          |
|-----------|---|---|---------|-----------------|----------|
| 4,124,024 | A |   | 11/1978 | Schwebel et al. |          |
| 4,913,699 | A |   | 4/1990  | Parsons         |          |
| 5,334,144 | A |   | 8/1994  | Alchas et al.   |          |
| 5,383,851 | A | * | 1/1995  | McKinnon et al. | ........... 604/68 |
| 5,730,723 | A |   | 3/1998  | Castellano et al. |        |
| 5,865,796 | A |   | 2/1999  | McCabe          |          |
| 5,899,880 | A | * | 5/1999  | Bellhouse et al. | ............ 604/70 |
| 6,010,478 | A | * | 1/2000  | Bellhouse et al. | ............ 604/70 |

(Continued)

FOREIGN PATENT DOCUMENTS

WO   WO 00/62846   10/2000

(Continued)

OTHER PUBLICATIONS

Kendall, et al., "The Gas-particle Dynamics of a High-Speed Needle-free Drug Delivery System," 22nd *International Symposium on Shock Waves*, pp. 605-610 (1999).

*Primary Examiner*—Kevin C. Sirmons
*Assistant Examiner*—Andrew Gilbert
(74) *Attorney, Agent, or Firm*—Kirkpatrick & Lockhart Preston Gates Ellis LLP

(57) ABSTRACT

A needleless syringe for subcutaneously delivering a therapeutic agent comprising a generally constant diameter elongate tubular nozzle and an inert gas reservoir thereto is described herein. The reservoir is advantageously mounted to the upstream end of the tubular nozzle through a contraction that is either gradual or sudden and wherein a membrane is positioned between the reservoir and the therapeutic agent.

51 Claims, 7 Drawing Sheets

U.S. PATENT DOCUMENTS

Figure 1:
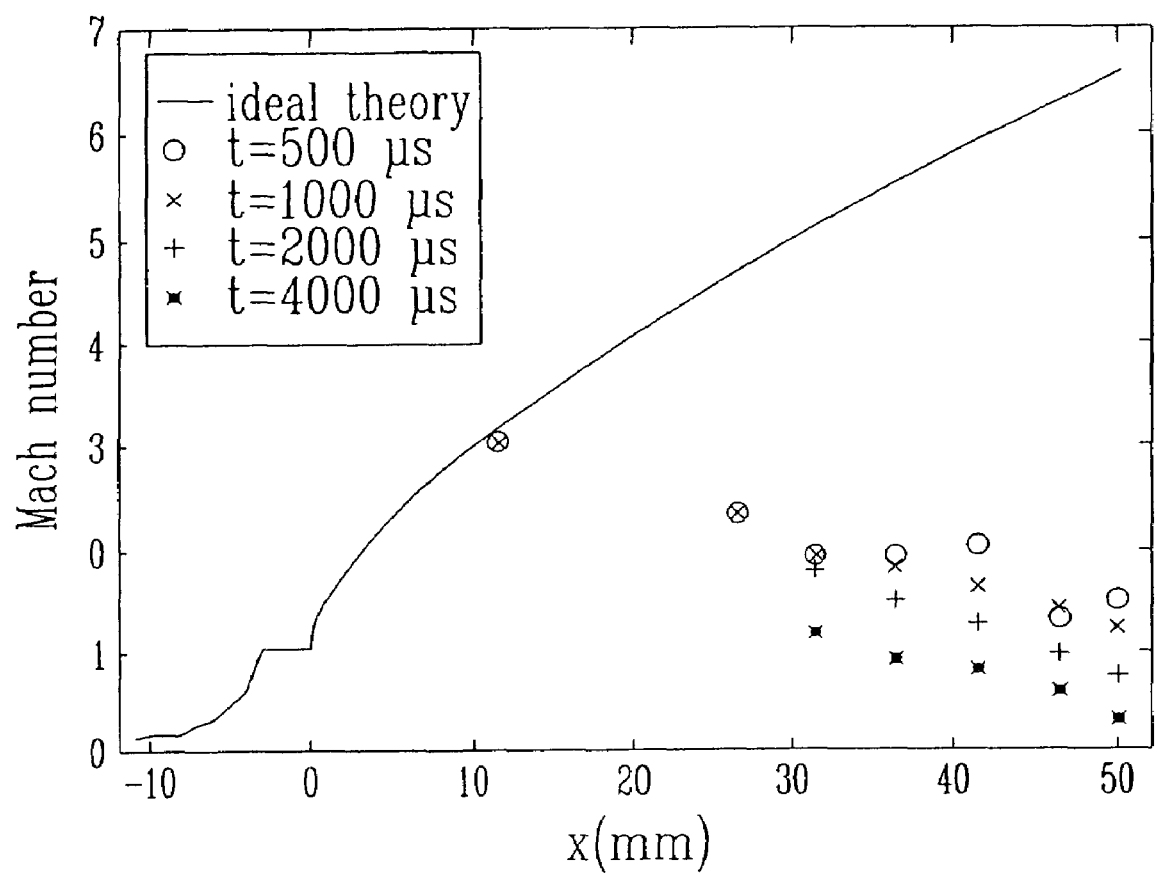

| | | | |
|---|---|---|---|
| 6,013,050 A * | 1/2000 | Bellhouse et al. | 604/70 |
| 6,475,181 B1 * | 11/2002 | Potter et al. | 604/68 |
| 6,592,545 B1 * | 7/2003 | Bellhouse et al. | 604/69 |
| 6,835,187 B2 | 12/2004 | Alexandre et al. | |
| 6,913,593 B1 * | 7/2005 | Alexandre et al. | 604/69 |
| 7,060,048 B1 * | 6/2006 | Nat et al. | 604/70 |
| 2002/0091353 A1 * | 7/2002 | Bellhouse et al. | 604/68 |
| 2004/0215135 A1 * | 10/2004 | Sheldrake et al. | 604/68 |

FOREIGN PATENT DOCUMENTS

| | | |
|---|---|---|
| WO | WO 01/05455 | 1/2001 |
| WO | WO 01/41840 | 6/2001 |
| WO | WO 02/26295 | 4/2002 |

* cited by examiner

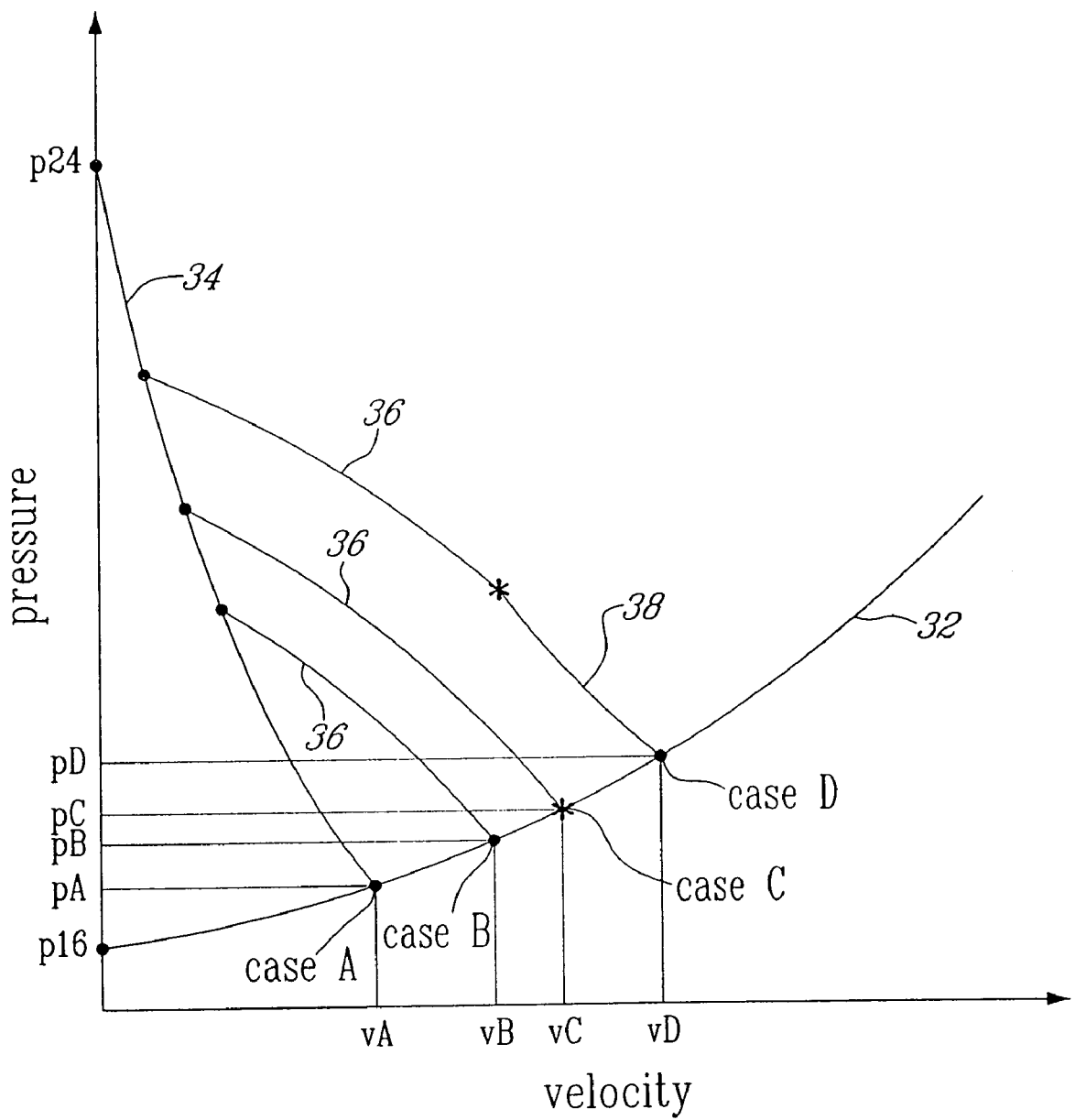
FIG_2D

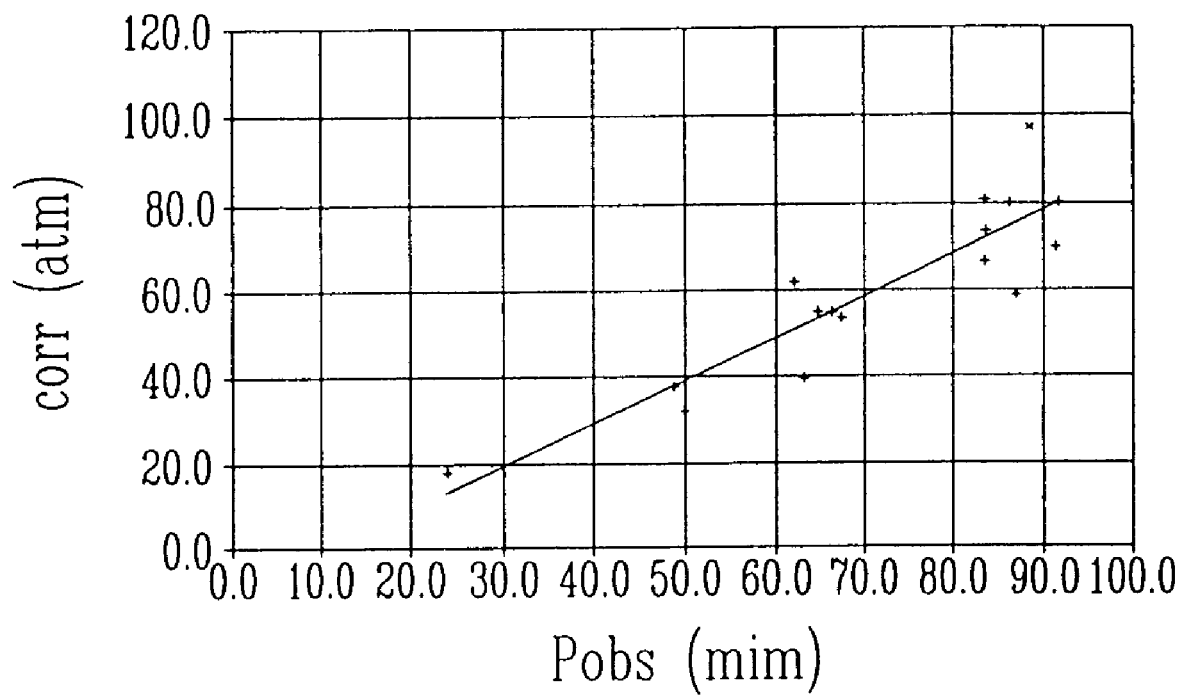
FIG_3
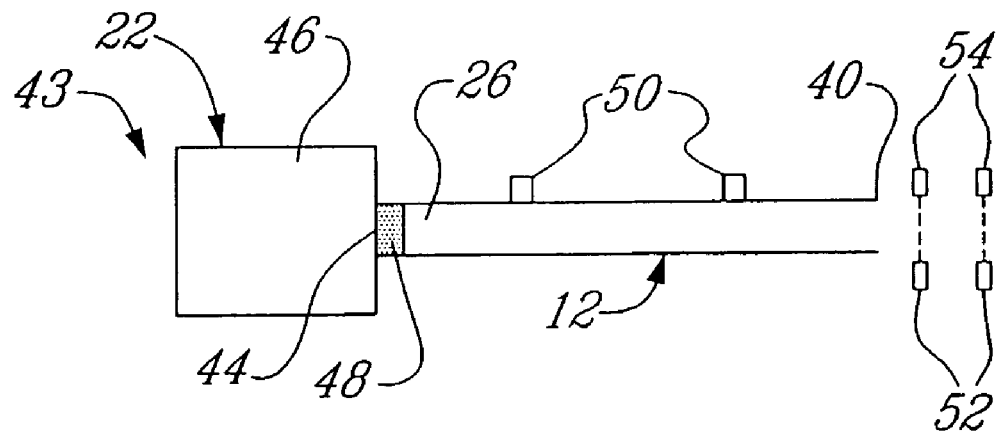
FIG_4

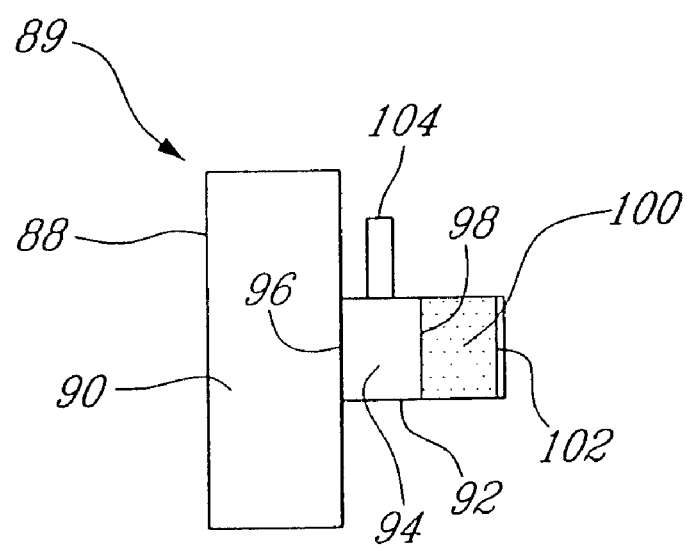
FIG_7A
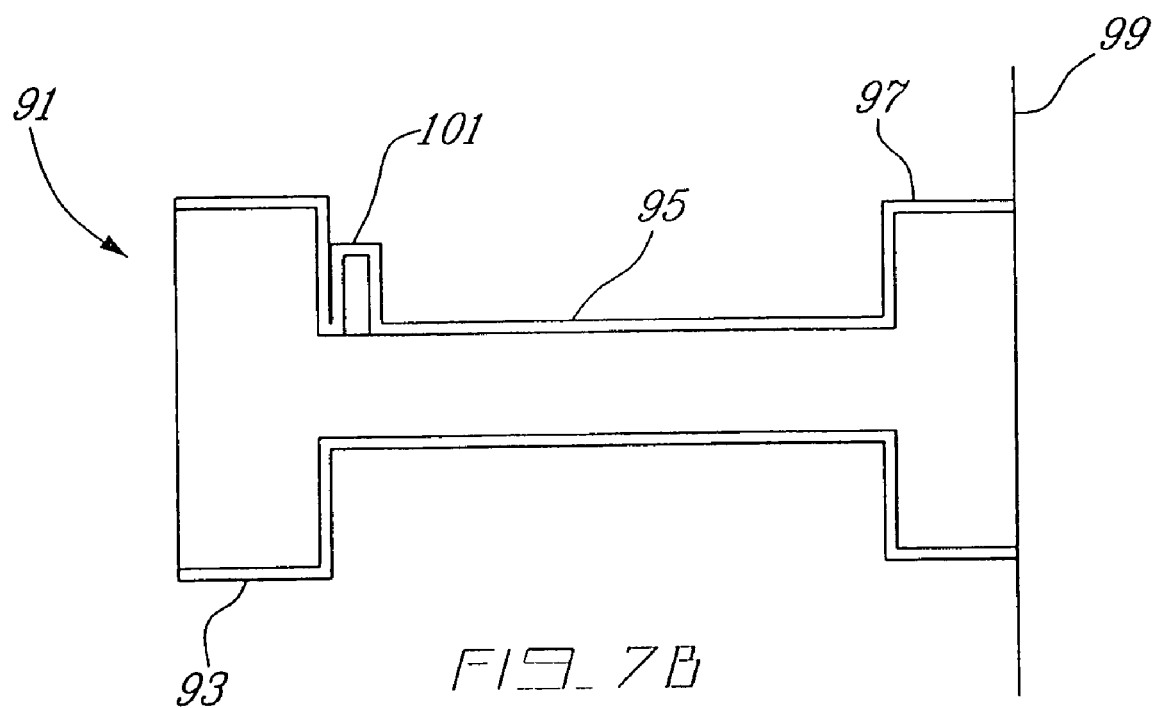
FIG_7B

NEEDLELESS SYRINGE FOR THE DELIVERY OF THERAPEUTIC AGENTS

CROSS-REFERENCE TO RELATED APPLICATIONS

This application is the national phase of International (PCT) Patent Application Ser. No. PCT/CA01/01491, filed Oct. 19, 2001, published under PCT Article 21(2) in English, which claims priority to and the benefit of Canadian Patent Application No. 2,324,045, filed Oct. 20, 2000. The disclosures of all of these applications are incorporated herein by reference.

FIELD OF THE INVENTION

The present invention relates to syringes. More specifically, the present invention relates to needleless syringes for the subcutaneous delivery of therapeutic agents.

BACKGROUND OF THE INVENTION

Needless syringes are known and have previously been described in the prior art.

In a broad sense, needleless syringes are used for the subcutaneous injection of therapeutic agents. An obvious advantage of the use of a needleless syringe, is the avoidance of physically perforating the epidermis. The therapeutic agents can present themselves in powder form. The active substances can be vaccines, anesthetics, medicaments, hormones, and genetic compounds, for example. These agents, while in the form of particles whose size is of the order of a few microns, are capable of penetrating the skin of a patient, due to the high velocity imparted upon them.

In their May 4, 1999 U.S. Pat. No. 5,899,880, Bellhouse et al. describe such a needleless syringe. Bellhouse et al. propose the use of a needleless syringe having a nozzle presenting a divergent downstream portion, in order to achieve a pseudo-steady-state gas expansion to accelerate the particle flow. The problem presented by this approach is double: (i) the particle flow is, in reality, not stationary, that is, it does not possess a steady state system and, (ii) the particle flow becomes detached from the inner wall of the divergent downstream nozzle, which reduces the expansion and hence the acceleration produced.

Additionally, the different needleless syringe embodiments described by Bellhouse et al., illustrate a membrane that ruptures when the pressure exerted upon it exceeds its threshold. Furthermore, a mechanism exploiting the direct rupture of the membrane as well as an approach without the use of a membrane was not explored.

Finally, Bellhouse et al. do not present concepts linking the particle dose to the gas reserve, other than the use of a quasi-static compression piston.

U.S. Pat. No. 5,865,796 issued on Feb. 2, 1999 to McCabe essentially describes a similar device, designed for the injection of genetic material in a laboratory setting.

Both of the above reported devices are capable of accelerating an inert gas, and hence the concomitant acceleration of the particles, through the expansion of the inert gas at high pressures, through a nozzle that has a convergent upstream section and a divergent downstream section (commonly referred to as convergent-divergent nozzle). Hence, one has to appreciate that the above-mentioned acceleration process functions at a constant or quasi-constant steady state, that is, once the waves resulting from the rupture of the membrane are no longer important. It becomes therefore obvious that in the Bellhouse et al. device, the particles will have been ejected from the device prior to the establishment of the so-called quasi steady state system.

The consequences of this observation are interesting, since researchers studying the Bellhouse system, carried out their optimization calculations based on the quasi steady state system hypothesis. Indeed, a recent publication (M. A. F. Kendall, N. J. Quinlan, S. J. Thorpe, R. W. Ainsworth and B. J. Bellhouse: *The gas-particle dynamics of a supersonic drug delivery system*. Book of Abstracts, $22^{nd}$ International Symposium on Shock Waves, London, 19-23 Jul. 1999) illustrates that because of their wrongful interpretation of this phenomenon, there exists an important discrepancy between the values predicted by the theoretical model and the observed experimental values, as can be observed in FIG. 1.

The graph of FIG. 1, which is labeled "prior art", is illustrative of a comparison between the calculated particle velocity profile and the measured particle velocity profile. It can be readily observed that the theoretical model predicts an exit velocity for the particles in the proximity of Mach 6, whereas the experimental observations illustrate a considerably lesser Mach velocity.

In their Jan. 25, 2001 PCT patent application published under no. WO 01/05455, Kendall & Brown describe a needless syringe which incorporates improvements on the Bellhouse system by correctly accounting for the starting process which thereby increases the predictability of the device. Kendall & Brown propose the use of a shock tube, comprised of two chambers of same or similar diameter, with a divergent nozzle attached to the downstream chamber. In their device, they explain that the particles are first set in motion via the production of a shock wave when the membrane initially separating the two chambers is ruptured and that further acceleration is then produced by the expansion of the gas in the divergent nozzle. In reality, this device is quite similar to that of Bellhouse et al., the only difference being the addition of a constant diameter downstream duct section before the divergent nozzle which increases the time delay between the undesirable nozzle starting phenomena and the particle acceleration phase.

Furthermore, the method for accelerating a dose of particles in a needleless device proposed by Kendall & Brown claims to comprise the production of a primary shock wave. It should be known that it is possible to carry a dose of particles with a device comprising a driver chamber and a duct section downstream of said driver chamber without producing a primary shock wave travelling in downstream direction in said duct section. Indeed, if the duct were evacuated, i.e., at zero absolute pressure, the opening of the closure means located between said driver chamber and said duct section would not, in this case, produce a primary shock wave travelling in a downstream direction in said duct section since there would be no pre-existing medium in said duct section for the shock wave to propagate into, but the dose of particles could still be accelerated by the expansion of the driver gas. The production of a primary shock wave, or any number of shock waves thereafter, is therefore not necessary to achieve particle acceleration.

The correct physical interpretation of these devices is rather obtained by examining the method of expansion of the gas contained within said driver section, which causes a gaseous piston to propagate in the downstream direction in said duct section thereby carrying particles in the same direction. By optimally producing this expansion, the performance of the device, as measured by particle velocity and uniformity of particle velocity achieved, can be predicted and maximized. This expansion can be produced through steady or quasi-steady means which usually utilize nozzles of convergent or divergent geometry. This expansion can also be produced through unsteady means, by sudden or gradual temporal changes in the flow properties, in which case unsteady trains of rarefaction waves are used.

In the device proposed by Bellhouse et al., the gaseous expansion mechanism is that of quasi-steady expansion using a converging-diverging nozzle. The shortcomings of using a divergent have been discussed above and in the patent application of Kendall & Brown (see FIG. 2 and associated discussion lines 28-32 p. 4 and lines 1-7 p. 3 of the Kendall & Brown document).

In the devices proposed by Kendall & Brown, there are either one or two driver gas expansion mechanisms. In all devices proposed by Kendall & Brown, there is an unsteady expansion produced by the opening of a closure means located between a driver chamber and a duct section located downstream of the driver chamber. The unsteady expansion waves can be seen as item 30 (comprising the leading wave 34) in FIG. 3 of the Kendall & Brown document. In most embodiments proposed by Kendall & Brown, there is also an additional quasi-steady driver gas expansion mechanism, achieved through the use of a divergent nozzle positioned downstream of said duct section. The shortcomings of using a divergent nozzle are in this case similar to those of the Bellhouse device. Kendall & Brown recognize that their proposed device could possibly work without having this divergent nozzle, but they fail to mention that to achieve the desired particle flow velocities without this nozzle, the required driver gas pressure would be very high thereby increasing the safety risks associated with the use of the device and also reducing the utility of the device since a very high pressure source of gas would be required. This is why they have to resort to a divergent nozzle in all embodiments of their invention.

In embodiment 5 of their proposed device, Kendall & Brown propose to have a driver chamber as having a larger area than the downstream duct section. However, in that proposal they have failed to recognize that a quasi-steady expansion would take place within the contraction and that for a sufficiently large area ratio a second unsteady expansion would be produced in the driver gas but downstream of the contraction.

It should be known that there exists other combinations of quasi-steady and unsteady gaseous expansion means that achieve a better performance than those in the Bellhouse and the Kendall & Brown devices.

OBJECTS OF THE INVENTION

An object of the present invention is therefore to provide an improved needleless syringe for the subcutaneous delivery of therapeutic agents.

SUMMARY OF THE INVENTION

More specifically, in accordance with the present invention, there is provided a needleless syringe for delivering therapeutic particles, wherein the syringe comprises a generally constant diameter elongate tubular nozzle having an upstream end and a downstream end, a triggering assembly mounted to the upstream end of the tubular nozzle, and a partition separating the triggering assembly from the tubular nozzle. The partition is designed to withstand large pressure differences between the elongate tubular nozzle and the triggering assembly, wherein a rupture of the partition results in the generation of a gaseous expansion capable of delivering the therapeutic particles at a velocity sufficient to subcutaneously deliver the particles.

In accordance with the present invention, there is provided a needleless syringe for delivering therapeutic particles comprising a triggering mechanism comprising a gas reserve containing a source of pressurized gas, a reservoir at essentially atmospheric pressure and, a release valve. The gas reserve is mounted at an upstream end of the reservoir and, the release valve separates the pressurized gas source from the reservoir such that opening of the release valve allows the pressurized gas to fill the reservoir until the partition ruptures, accelerating the therapeutic particles towards the downstream end of the nozzle.

Also, in accordance with the present invention, there is provided a needleless syringe for delivering therapeutic particles comprising a triggering mechanism comprising a first reservoir filled with a first pressurized gas; a second reservoir filled with a second gas at a lower pressure relative to the first gas and mounted downstream from the reservoir and including an orifice that can be opened to the atmosphere; a first membrane separating said the reservoir from the second reservoir; and a second membrane separating the second reservoir from the tubular nozzle. Opening the orifice to the atmosphere results in a pressure-drop in the second reservoir resulting in the rupturing of the first membrane whereby the first pressurized gas fills the second reservoir in turn rupturing the second membrane, thus accelerating the therapeutic particles towards the downstream end of the nozzle.

Also, in accordance with the present invention, there is provided a needleless syringe for delivering therapeutic particles comprising a triggering mechanism comprising a compressed gas reserve; a reservoir having a first chamber filled with a gas at atmospheric pressure and a second chamber filled with a gas at atmospheric pressure; a piston separating the first chamber from the second chamber; a release valve separating the compressed gas reserve from the first chamber; and a membrane separating the gas of the second chamber from the tubular nozzle. Opening the release valve allows the compressed gas to fill the first chamber, pushing the piston into the second chamber compressing the gas in the second chamber until the membrane ruptures, thus accelerating the therapeutic particles towards the downstream end of the nozzle.

Also, in accordance with the present invention, there is provided a needleless syringe for delivering therapeutic particles comprising a triggering mechanism comprising a cylindrical reservoir including a downstream chamber filled with a gas at essentially atmospheric pressure and an upstream chamber; a piston attached to a compressed spring, the piston separating the upstream chamber from the downstream chamber; and a membrane separating the gas of the upstream chamber from the tubular nozzle. Releasing the compressed spring pushes the piston into the upstream chamber thereby compressing the gas in the upstream chamber causing the membrane to rupture, thus accelerating the therapeutic particles towards the downstream end of the nozzle.

In accordance with the present invention, there is also provided a method for delivering therapeutic particles comprising the steps of providing a generally constant diameter elongate tubular nozzle having an upstream end and a downstream end; mounting a triggering assembly to the upstream end of the nozzle via a contraction, the triggering assembly being separated from the upstream end of the nozzle by a partition; positioning a source of particles in the upstream end of the tubular nozzle; and activating the triggering assembly producing a gaseous expansion accelerating the particles toward a target surface at a velocity sufficient to enter the target surface.

Also, in accordance with the present invention, there is provided a method for delivering therapeutic particles comprising the steps of providing a gas reserve containing a source of pressurized gas, providing a reservoir at essentially atmospheric pressure and having a diameter larger than the diameter of the nozzle; and providing a release valve. The gas reserve is mounted to the upstream end of the reservoir and the release valve separates the pressurized gas from the reservoir. The activating step includes the opening of the release valve to allow the pressurized gas to fill the reservoir until the partition ruptures to thereby accelerate the therapeutic particles towards the downstream end of the nozzle.

Also, in accordance with the present invention, there is provided a method for delivering therapeutic particles comprising the steps of providing a first reservoir filled with a first pressurized gas; providing a second reservoir mounted downstream from the first reservoir and including an orifice, the second reservoir being filled with a second gas at a lower pressure relative to the first gas; providing a first membrane separating the first reservoir from the second reservoir; and providing a second membrane separating the second reservoir from the tubular nozzle. The activating step includes opening the orifice to cause a pressure-drop in the second reservoir resulting in the rupturing of the first membrane whereby the first pressurized gas fills the second reservoir in turn rupturing the second membrane, thus accelerating the therapeutic particles towards the downstream end of the nozzle.

Also, in accordance with the present invention, there is provided a method for delivering therapeutic particles comprising the steps of providing a compressed gas reserve; providing a reservoir having a first chamber filled with a gas at atmospheric pressure and a second chamber filled with a gas at atmospheric pressure; providing a piston separating the first chamber from the second chamber; providing a release valve separating the compressed gas reserve from the first chamber; and providing a membrane separating the gas of the second chamber from the tubular nozzle. The activating step includes opening the release valve to allow the compressed gas to fill the first chamber pushing the piston into the second chamber, compressing the gas in the second chamber until the membrane ruptures, thus accelerating the therapeutic particles towards the downstream end of the nozzle.

Also, in accordance with the present invention, there is provided a method for delivering therapeutic particles comprising the steps of providing a cylindrical reservoir including a downstream chamber filled with a gas at essentially atmospheric pressure and an upstream chamber; providing a piston attached to a compressed spring and separating the upstream chamber and the downstream chamber; and providing a membrane separating the gas of the upstream chamber from the tubular nozzle. The activating step includes releasing the compressed spring to push the piston into the upstream chamber thereby compressing the gas in the upstream chamber causing the membrane to rupture, thus accelerating the therapeutic particles towards the downstream end of the nozzle.

Other objects, advantages and features of the present invention will become more apparent upon reading of the following non-restrictive description of preferred embodiments thereof, given by way of example only with reference to the accompanying drawings.

BRIEF DESCRIPTION OF THE DRAWINGS

In the appended drawings:

FIG. 1 which is labeled "Prior Art" is a diagram comparing the calculated particle velocity profile and the measured particle velocity profile;

FIG. 2A is a schematic outline of a syringe illustrating the various elements of the present invention in a static mode;

FIG. 2B is a schematic outline of the syringe of FIG. 2A, illustrating the various elements of the present invention in a dynamic mode;

FIG. 2C is a schematic outline of the trajectories of the particle flow and the trajectories of the various waves generated by the syringe of FIG. 2A;

FIG. 2D is a graphical representation in pressure-velocity space of the gas dynamics phenomena taking place in the various needleless syringe configurations.

FIG. 3 is diagram illustrating the observed pressure in function of the corrected pressure;

FIG. 4 is a schematic outline of an experimental syringe assembly, according to one aspect of the present invention;

FIG. 5A is a schematic outline of a needleless syringe, according to a first embodiment of the present invention;

FIG. 5B is a schematic outline of a particle dose to be used in the syringe of FIG. 5A;

FIG. 5C is a schematic outline of an alternative particle dose to be used in the syringe of FIG. 5A;

FIG. 6 is a schematic outline of a disposable needleless syringe, according to a second embodiment of the present invention;

FIG. 7A is a schematic outline of a self-contained particle dose/pressurized source assembly according to a third embodiment of the present invention;

FIG. 7B is a schematic outline of a reusable device to be used with the self contained assembly of FIG. 7A;

FIG. 8 is a schematic outline of a needleless syringe, comprising an unengaged piston, according to a fourth embodiment of the present invention; and FIG. 9 is a schematic outline of a needleless syringe, comprising a spring compressing a piston in a non-stationary manner, according to a fifth embodiment of the present invention.

DESCRIPTION OF THE PREFERRED EMBODIMENT

The needleless syringe of the present invention is essentially designed to deliver particles of a therapeutic agent at velocities sufficiently high, such that they can penetrate the epidermis or other target tissue of a patient and can produce the desired medical effect. As discussed hereinabove, the advantages of using a needleless syringe are readily apparent, the two principal advantages being a reduced risk of infection, and the essentially complete elimination of pain and fear for the case of transdermal delivery.

Generally stated, the present invention aims at accelerating particles of microscopic size, by means of a non-stationary expansion of an inert gas at high pressure.

FIG. 2A schematically shows the various parts of a needleless syringe 10, to illustrate the concept of the present invention. The needleless syringe 10, comprises a generally constant diameter tubular nozzle 12, near the target 14, e.g. the skin of a patient. The nozzle 12 is filled with an inert gas or air 16, under atmospheric or other conditions (it can also be completely evacuated). The upstream end 18 of the nozzle 12 contains particles of a therapeutic agent 20. A triggering assembly, including a reservoir 22 of an inert gas 24 under high pressure, having a diameter larger to the tubular nozzle 12 is mounted to the upstream end 18 of the nozzle, the downstream end 26 of the nozzle 12 being designed to be brought near the target 14. The reservoir 22 can be pre-loaded with pressurized gas.

Figure 2A:
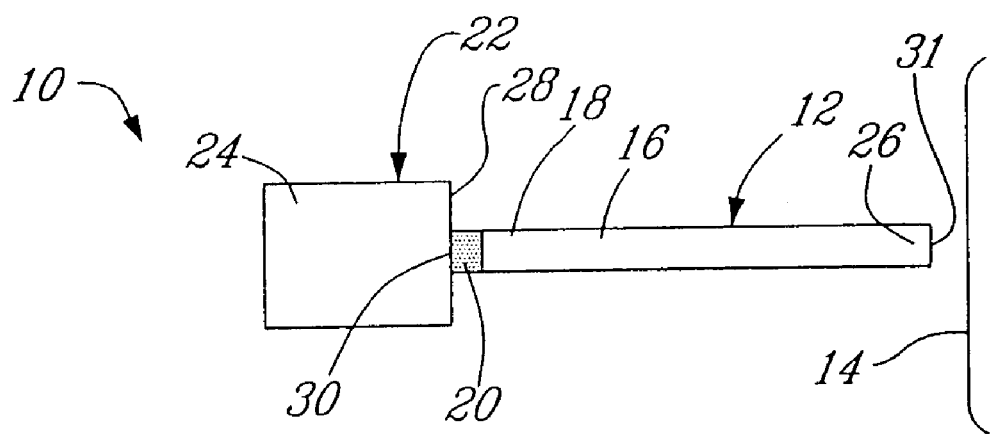

The reservoir 22 and the tubular nozzle 12 are linked through a contraction 28 that is either sudden (as shown in FIG. 2A) or gradual (not shown). The reservoir 22 is separated from the tubular nozzle by a partition 30 sufficiently resistant to withstand the pressure difference existing between the reservoir 22 and the particles 20 in the tubular nozzle 12, which are essentially under atmospheric or other conditions.

To activate the needleless syringe 10, the partition 30 is ruptured or suddenly removed, allowing the pressurized gas 24 contained within the reservoir 22 to expand into the tubular nozzle 12.

Figure 2B:
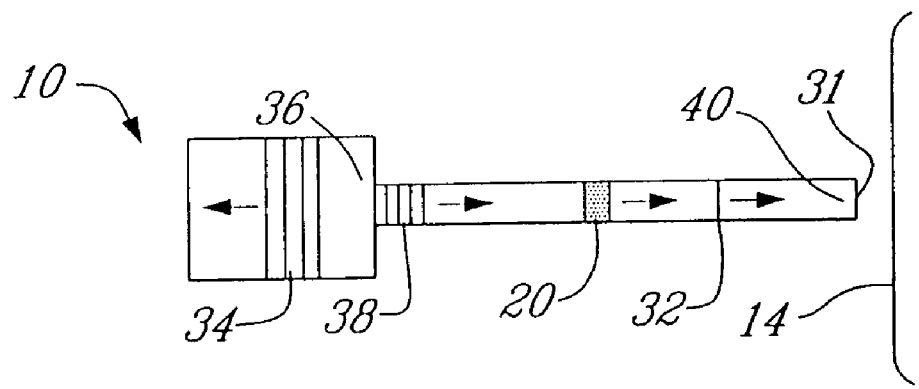
Figure 2C:
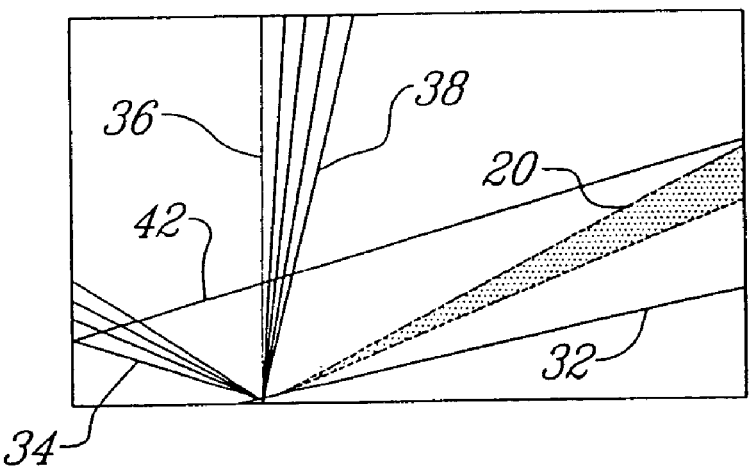

As can be seen from FIG. 2B, the sudden removal or rupture of the partition 30 immediately produces i) a shock wave 32 in the tubular nozzle 12; ii) non-stationary expansion waves 34 in the reservoir 22; and if the diameter of the reservoir is sufficiently large compared to that of the tubular nozzle iii) a stationary expansion wave 36 in the contraction 28 and iv) non-stationary expansion waves 38 in the tubular nozzle 12. It should be noted that if the tubular nozzle 12 were evacuated, the shock wave 32 would not be produced but the rest of the wave pattern would essentially be the same.

The rupture of the partition additionally generates non-stationary waves traveling in the upstream direction of the reservoir 22. These non-stationary expansion waves reflect from the upstream end of the reservoir, after which they start to travel in a downstream direction. The non-stationary expansion waves 38 produce an essentially steady high velocity flow in the downstream direction 26 of the tubular nozzle 12, wherein the flow carries the particles of a therapeutic agent in the same downstream direction.

These waves produce an almost instantaneous acceleration of the gas contained within the tubular nozzle 12 and of the gas contained within the reservoir 22. The accelerated gas in the tubular nozzle 12, moving at high velocity, carries the therapeutic agent 20 towards the exit of the nozzle 40 and hence towards the target 14. The particles 20 are accelerated from an initial position downstream from the partition 30.

A pattern of stationary and non-stationary expansion waves is generated at the downstream 26 end of the tubular nozzle 12, when the high velocity flow reaches the exit 40 of the tubular nozzle 12. The essentially steady high velocity flow terminates when the leading front of the reflected non-stationary expansion waves reaches the downstream end of the nozzle. Additionally, the high velocity flow exits the downstream 26 end of the tubular nozzle 12, carrying an essentially spatially uniform and parallel particle velocity distribution.

In the present invention, expansions 34, 36 and 38 generated upon rupturing or removal of the partition are primarily responsible for the observed acceleration of the gases contained within the device. It is believed possible to obtain a substantial gain in performance, when the internal diameter of the reservoir is largely superior to the diameter of the tubular nozzle. In this case, the expansion of the driver gas, and therefore the particle velocity, would be increased while keeping the pressure ratio between the reservoir and the tubular nozzle the same.

If the velocity of the gas and hence of the particles 20 is sufficiently high, i.e. in the order of 100-2000 m/s, the particles 20 will be capable of penetrating the target 14 to a sufficient depth, such that it will be ingested by the patient to then produce the desired medical effect.

FIG. 2C illustrates a diagram of the trajectories of the particle flow in the tubular nozzle 12 as well as in the reservoir 22, using the same notation for the generated waves as in FIG. 2B. It can be readily observed that the particles of the therapeutic agent 20 are carried by a quasi steady stream of gas at high velocity produced in the region between the shock wave 32 and the reflected expansion. Additionally, it can be observed that the required quantity of inert gas 24 is determined by the length of the reservoir 22, whose length is itself determined in order to avoid a possible return of reflection waves 42, prior to the exit of the therapeutic agent 20 from the tubular nozzle 12.

The fluid dynamics taking place in the device from the time of partition removal can best be computed and understood with the help of a pressure-velocity (p-V) diagram. With such a graphical tool, the specific features of the different possible configurations can clearly be ascertained. FIG. 2D shows the pressure velocity diagram for devices having various ratios of reservoir diameter versus tubular nozzle diameter for a given fixed pressure ratio between these two sections.

If the internal diameter of the reservoir is the same as that of the tubular nozzle, only the non-stationary expansion waves 34 will be produced. In the pressure-velocity diagram of FIG. 2D, this is shown as "Case A". It is seen that the solution is obtained by the intersection of the curve representing all possible final states produced by a shock wave 32 in the tubular nozzle with the curve representing all possible final states produced by unsteady expansion waves 34 in the reservoir gas. It is seen that Case A (same internal diameter for reservoir and tubular nozzle) yields a resulting gas velocity, $V_A$ thus particle velocity, which is fairly low.

However, as the reservoir internal diameter is increased with respect to that of the tubular nozzle, a quasi-steady expansion 36 would appear in the gradual or instantaneous contraction region, thereby producing higher flow velocities. This is illustrated in FIG. 2D as "Case B" where, the combination of the unsteady expansion 34 and the quasi-steady expansion 36 produces a final state at higher velocity $V_B$.

Interestingly, as the reservoir internal diameter is further increased with respect to that of the tubular nozzle, this quasi-stationary expansion would become stronger and therefore produce higher flow velocities up to the a point when the flow at the entrance of the tubular nozzle would become sonic (i.e., Mach number equal to 1). This is indicated in FIG. 2D as "Case C" and, according to the usual convention, the sonic state is indicated in FIG. 2D by an asterisk.

For physical reasons, further increasing the internal diameter of the reservoir does not produce a higher quasi-steady expansion past the sonic point within the contraction but instead a new unsteady train of expansion waves 38 would appear in the tubular nozzle. Actually, these waves are propagating upstream with respect to the reservoir gas but since the latter flows downstream at sonic, or higher, flow velocities, the expansion 38 is being swept downstream into the tubular nozzle. In the pressure-velocity diagram of FIG. 2D, this is shown as "Case D". Obviously, the highest flow velocities for a given pressure ratio are produced in this configuration.

The advantages of using a reservoir with a large internal diameter as compared to that of the tubular nozzle are thus apparent from FIG. 2D, where it can be seen that, for the same pressure ratio between the reservoir and the tubular nozzle, higher flow and particle velocities are thus produced. To produce a particle stream at a given velocity, the present invention therefore requires a lower pressure driver gas than that of the prior art without the need to use a divergent nozzle.

Generally stated, the prior art failed to recognize that a quasi-steady expansion would take place within the contraction and that for a sufficiently large area ratio a second unsteady expansion would be produced in the driver gas but downstream of the contraction. This is the mechanism that is exploited herein.

Based on these flow mechanisms, a theoretical model to calculate the gas flow in the syringe of the present invention was established in order to optimize the syringe's parameters and to enhance its performance. More specifically, the theoretical model suggests that the velocity produced in the tubular nozzle 12, and therefore the velocity of the particles 20 at the exit of the nozzle 12, is essentially a function of:

the pressure ratio between the gas of the reservoir 24 and the gas 16 of the tubular nozzle 12;

the thermodynamic properties of the gas of the reservoir 24, and the gas 16 of the tubular nozzle 12, more specifically the speed of sound (which is temperature dependent);

the specific heat ratio of the two gases;

to a certain extent, the ratio of the length of the reservoir 22 and the length of the tubular nozzle 12; and the diameter ratio of the reservoir 22 and of the tubular nozzle 12.

It can be seen from FIG. 2D that the resulting high flow velocities produced with the present invention are also accompanied by a large pressure increases in the tubular nozzle. This is a further advantage of the present device which produces high particle velocities without the further pressure reduction caused by divergent nozzles.

Depending on the initial pressure ($P_{16}$) of the gas 16 within the tubular nozzle 12, the pressure at the exit 40 of the tubular nozzle during the operation of the device could be lower, equal or larger than the ambient (e.g., atmospheric) pressure near the target.

If the pressure at the exit 40 is lower than ambient (i.e., the so-called overexpanded case), then normal or oblique shock waves would appear at the exit to bring the pressure up to the required ambient pressure, at the cost of a reduction in flow velocities. If the pressure at the exit would be higher than ambient (underexpanded case), a steady expansion fan (i.e., Prandtl-Meyer expansion) would be produced outside the exit 40 to bring the pressure back down, with a resulting potentially beneficial increase in flow velocity. One can therefore see that it is better to have exit pressures matched with or higher than ambient to avoid the reduction in flow velocities associated with the shock waves present in the overexpanded case. Since the particle acceleration method described in the present invention produces large pressure ratios at the tube exit as compared to previous ones, this is a further advantage of the present invention.

Because the present invention produces exit pressures ($P_D$) that are higher than the initial pressure ($P_{16}$) of the gas 16 contained within the tubular nozzle 12, having the gas 16 at the same pressure as the ambient pressure around the target 14 therefore guarantees that the undesirable overexpanded case is never produced with the present invention.

The matched case (i.e., same nozzle exit pressure as ambient pressure) could be produced by having the gas 16 at a lower initial pressure than ambient. To achieve this, a thin closure element 31 could optionally be mounted to the nozzle exit 40 to support the pressure difference, and this closure means would be removed or break when impacted by the arrival of the flow at the exit 40.

If the tubular nozzle exit 40 were in direct contact with the target 14, the arrival of the shock wave 32 at the target 14 would produce a reflected shock wave back into the tubular nozzle thereby slowing the flow down to a rest. To prevent this from occurring, the exit 40 of the nozzle is to be positioned at a predetermined distance from the target, preferably by using a nozzle extension having a larger internal diameter than that of the nozzle. This nozzle extension, also called a spacer, could be shaped in such a way as to also serve as a silencer to reduce the noise produced by the operation of the device 10.

FIG. 3 is illustrative of a comparison between the theoretical model and the values measured by the experimental assembly illustrated in FIG. 4 and described hereinbelow.

This comparison is expressed in terms of the pressure measured in the high pressure reservoir 22 at the time of rupture of the membrane 44 (Pobs), and the so-called corrected pressure (Pcorr), that is, the pressure value required by the theoretical model in order to obtain the observed velocity at the exit 40 of the tubular nozzle 12. One can readily observe from this comparison that since Pobs<Pcorr, the velocity at the exit 40 of the tubular nozzle 12 is generally less important than the velocity predicted by the experimental model (Pobs), but that this discrepancy is minimal and essentially constant throughout the range of velocities. This illustrates that it is possible to calculate with a high degree of dependability, the velocity of the particles at the exit 40 of the tubular nozzle 12 in function of the geometric and dynamic parameters of the device.

The theoretical model was validated by experimental testing of the primary configuration of the device. The experimental assembly, as illustrated in FIG. 4, essentially emulates the geometry illustrated in FIG. 2, the latter being used for the above-mentioned theoretical calculations.

The experimental syringe 43 comprises a partition 44 made of a Mylar membrane, separating the reservoir 22 from the tubular nozzle 12. The partition 44 punctures when the pressure in the reservoir 22 is sufficiently increased. The reservoir 22 has an internal diameter of 15.7 mm and is filled with an inert gas 46, preferably helium, at pressures ranging from 20 to 80 atmospheres.

The tubular nozzle 12 has an internal diameter of 4.9 mm, is exposed to the atmosphere and is charged with about 2 to 3 grams of an yttrium oxide powder 48 having a nominal particle size inferior to 10 microns. The powder 48 is positioned at the upstream end of the tubular nozzle 12, in direct contact with the Mylar partition 44.

The trajectory of the various waves generated in the tubular nozzle 12 upon puncturing of the membrane 44, was measured with the help of two piezoelectric pressure detectors 50. The velocity of the powder exiting the tubular nozzle 12, was determined with a system composed of diode lasers 52 and photo-detectors 54, positioned at the exit 40 of the tubular nozzle 12.

This study therefore illustrates that a viable concept is developed for the injection of therapeutic agents. Additionally, a theory capable of predicting the performance of the syringe is developed allowing for further optimization of the present invention.

Figure 5A:
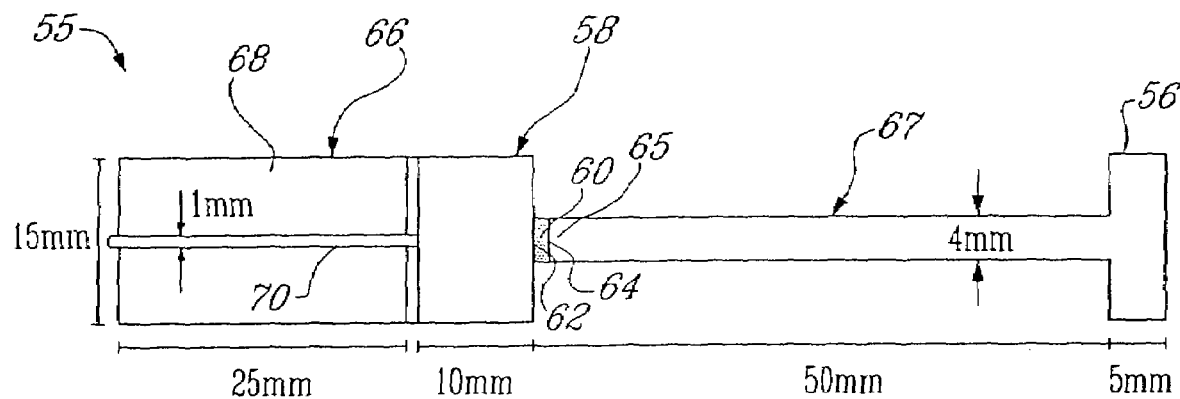

Turning now to FIG. 5A, a syringe 55 according to a first embodiment of the present invention will be described. The syringe 55, whose approximate dimensions are indicated in FIG. 5A, includes a reservoir 58 that is initially at atmospheric pressure, and a particle dose 60. The particle dose 60 comprises an upstream membrane 62 and a downstream membrane 64, containing the particle dose therebetween. The particle dose 60 is positioned in the upstream end 65 of the tubular nozzle 67 such that its upstream membrane 62 is directly adjacent to the reservoir 58. The upstream membrane 62 is designed to support the pressure differences between the reservoir 58 and the tubular nozzle 67. The triggering assembly of the syringe 55 additionally comprises a gas reserve 66 containing a high pressure inert gas 68 positioned upstream from the reservoir 58, as well as a release valve 70, separating the reservoir 58 and the gas reserve 66.

It is to be noted that the downstream end 56 of the nozzle 67 is enlarged to form a spacer and an optional silencer. The spacer is shaped so as to create a substantially normal wave near the surface of the target. The substantially normal wave decelerates the particles such that a radially uniform particle velocity distribution is obtained. Additionally, the release valve includes a small diameter orifice controlling the flow rate of the pressurized gas into the reservoir upon opening of the release valve.

It is also to be noted that the measurements given in FIG. 5A are given as an illustrative example only and could be modified without departing from the present invention. Additionally, syringe 55 could also further comprise a silencer mounted to the downstream end 56 of the tubular nozzle 67.

Figures 5B, 5C:
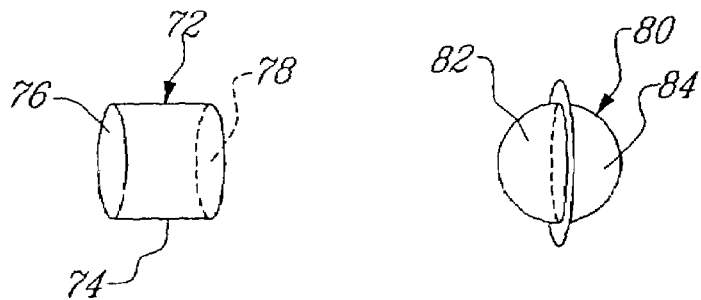

As can be observed in FIGS. 5B and 5C, various shapes of particle doses may be used. More specifically, FIG. 5B depicts an example of a generally cylindrical particle dose 72 that is contained within an essentially cylindrical envelope 74, confined by an upstream membrane 76 and by an downstream membrane 78. Furthermore, FIG. 5C illustrates a particle dose 80 confined by an upstream hemispheric membrane 82, and a downstream hemispheric membrane 84, the two hemispheric membranes generally defining a sphere. The membranes 76, 78, 82 and 84 can be arranged to rupture in a controlled manner due to indentations or scoring (not shown) in their surfaces.

Returning to FIG. 5A, the syringe 55 is triggered by a release valve 70, enabling a high pressure inert gas 68 previously contained in a gas reserve 66 to fill the reservoir 58 until a sufficiently elevated pressure is reached, causing the upstream membrane 62 to rupture, followed by the rupture of the downstream membrane 64 (both being part of the particle dose 60). When the upstream membrane 62 and the downstream membrane 64 rupture, the particle dose 60 is subjected to a burst of high pressure gas produced by the various steady and unsteady waves and is accelerated through the tubular nozzle 67. A non-illustrated return mechanism closes the release valve 70, in order to avoid any loss and squandering of inert gas 68 from the reserve 66. The volume and elevated pressure of the gas contained in the reserve 66, would allow for several consecutive injections. The gas reserve 66 could have been previously filled with a gas cylinder or with a disposable high pressure gas container (not illustrated). The size of the orifice of the release valve 70 would be small in order to decouple the wave phenomenon taking place in reservoir 58, from the gas reserve 66.

It is to be noted that FIG. 5A is schematic.

Syringe 55, according to a first embodiment of the present invention, can be modified in order to facilitate its ease of operation as well as to increase its capabilities. More specifically, the aspects that warrant particular attention are the membranes, the particle dose, the source of compressed gas and the sterility.

Control of the velocity of the particles impacting a surface is achieved by selecting the initial physical properties of the gases comprised in the reservoir and in the nozzle.

The pressure ratio that exists between the reservoir 58 and the tubular nozzle 67 just before membrane rupture, partially determines the velocity of the particle dose 60, and for a given upstream membrane 62, this ratio is constant. The simplicity of operation constitutes the main advantage of directly introducing compressed gas into the reservoir 58 until rupture of the upstream membrane 62 once a predetermined pressure is reached.

For any given dose of particles of a given size distribution, control of the velocity of the particles is lost and therefore control is also lost over the penetrating depth of the particles, since the penetration depth is directly a function of their velocity. It would be therefore be desirable to better control the rupturing pressure. This is possible by either replacing the upstream membrane 62 with a quick release valve or by directly puncturing the membrane. The implementation of either of these proposed methods, implies a syringe that is triggered by a previously determined gas pressure in the reservoir 58.

It is to be noted that directly rupturing the upstream membrane 62 is also envisioned by the present invention. Indeed, it is possible to use a circularly shaped knife, positioned upstream from the upstream membrane 62, and having a diameter identical to the inside of the tubular nozzle 67. Additional concepts, for example involving quick release valves comprising a radially moving guillotine or an axially moving door, are also possible. For all the above-mentioned examples, the reservoir 58 is advantageously equipped with a gas pressure indicator that is either quantitative or qualitative.

In the various concepts involving the use of quick release valves, the particle dose 60 does not require the incorporation of a membrane of predetermined resistance, in fact, the presence of a membrane is not necessarily required.

As far as the disadvantages of a single dose device are concerned, several multi-dose concepts are possible by calling upon cartridges having a linear geometry (like a semi-automatic pistol) or a circular geometry (like a revolver). With these concepts, time losses associated with charging the device would be avoided, which could prove very useful in large scale vaccination campaigns for example.

The operation of the needleless syringe 55 requires a source of compressed inert gas, preferably helium, at pressures that can reach up to 100 atmospheres. The source of inert gas can potentially be a commercial gas cylinder, equipped with an appropriate pressure regulator valve. An additional source can be a conventional pressurized disposable inert gas ampoule.

It is possible to eliminate the need for an external source of compressed inert gas, by providing for a particle dose wherein a gas reservoir comprising a compressed inert gas at a desired pressure is already incorporated. Additionally, such a concept could also be extended to provide for a particle dose comprising an integral tubular nozzle. An entirely disposable device, with the exception of the spacer/silencer, which can be sterilized and re-used, would then be provided.

Figure 6:
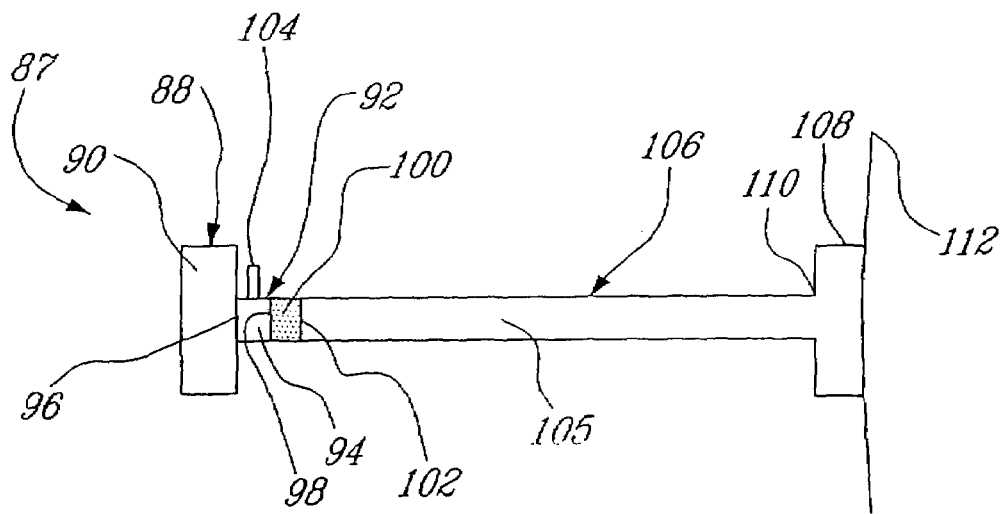

Turning now to FIG. 6 a disposable self-contained needleless syringe 87 according to another embodiment of the present invention will be described. The needleless syringe 87, takes advantage of a particle dose that comprises three membranes and two reservoirs of compressed gas.

The triggering assembly of the disposable needleless syringe 87 comprises a first large diameter reservoir 88 that is filled with a high pressure inert gas 90 and that is positioned upstream from a second small diameter reservoir 92, filled with a gas 94, at a pressure intermediate between the gas 90 in the first reservoir 88 and the pressure within the particle dose 100.

A first membrane 96 separates the first reservoir 88 from the second reservoir 92. This first membrane 96 supports the pressure difference that exists between the gas 90 in the first reservoir 88 and the gas 94 in the second reservoir 92. A second membrane 98 separates the second reservoir 92 from the therapeutic agent 100 and supports the pressure difference between the gas 94 in the second reservoir 98 and the pressure within the particle dose 100. The gas 94 in the second reservoir 92 is at a pressure above atmospheric pressure. Finally, a third membrane 102, isolates the therapeutic agent 100 from the gas 105 in the tubular nozzle 106, and therefore depending on the pressure difference between the dose 100 and the gas 105, may or may not support any pressure differential.

The disposable needleless syringe 87 is triggered by temporarily opening the orifice 104 to the atmosphere (see FIG. 6), thereby venting the gas 94 to the atmosphere, which results in a pressure drop in the second reservoir 92, with a concomitant increase in the pressure difference across the first membrane 96. This pressure difference increase on the first membrane 96 inevitably results in its rupture, in turn exposing the two remaining membranes to a surge in pressure and their subsequent rupture, thereby establishing the desired flow field which leads to the acceleration of the therapeutic agent 100 through the tubular nozzle 106 and the spacer/silencer 108, mounted on the distal end 110 of the tubular nozzle 106 towards the target 112. The orifice 104 is small so as to decouple the flow phenomena taking place within the reservoir 88 and the tubular nozzle 106 from the atmosphere, once the device is triggered.

Turning now to FIGS. 7A and 7B, another embodiment of the present invention will be described. FIG. 7A illustrates a disposable particle dose/pressurized gas source assembly 89 similar to the syringe 87 of FIG. 6 but lacking the tubular nozzle and the spacer/silencer. This entire disposable cartridge assembly 89 could then be inserted into a reusable device 91, illustrated in FIG. 7B, comprising a large diameter housing 93 connected to a tubular nozzle 95 itself attached to a spacer/silencer 97. By temporarily opening of lateral orifice 104, either using a quick-release valve 101, puncturing the side of the second reservoir 92 or other suitable means, the gas at intermediate pressure 94 within the second reservoir 92 of the charged assembly 89 is vented to the atmosphere, thereby successively triggering the rupture of membranes 96, 98 and 102 and establishing the desired wave phenomena within the device and accelerating the particles into the tubular nozzle 95 towards the target 99.

As discussed hereinabove, the disposable cartridge assembly 89 could also incorporate the tubular nozzle. In this case, the reusable device would comprise only the large diameter housing 93 attached via a tubular region 96 of larger size than that of the tubular nozzle to the spacer/silencer 97.

For a system comprising the disposable charged assembly 89 or variations thereof and the reusable device 91, or variations, it is envisioned that the reusable device 91 could be similar to a revolver or a semi-automatic pistol, with the mechanism 101 for opening the orifice 104 incorporated into the revolver/pistol type device and the "gun barrel" being replaced by the tubular nozzle 95 or tubular housing 96, with the silencer spacer at its distal end. For the revolver-type device, the disposable cartridges would be arranged around the periphery of a cylindrical barrel and upon firing a spent cartridge would be rotated away to be replaced with a loaded cartridge. After firing all the cartridges within the barrel, the spent cartridges would be replaced with loaded ones. For a pistol-type device, the cartridges would be arranged in a linear array. For these revolver/pistol type devices, the target and the spacer/silencer would be sterilized prior to firing. Since this can be done rapidly through chemical agents, for example, such devices would allow for a minimal delay between each firing, which could prove useful in large volume applications such as vaccination campaigns. Another way to ensure sterility would involve replacing the spacer/silencer after each shot.

Another method, aiming to avoid the use of a high pressure source of an inert gas, is to directly incorporate into the needleless syringe, a gas compression mechanism. It is possible to adjoin a low pressure inert gas reservoir to the particle dose, which leaves the compression of the inert gas to be accomplished. Two concepts, based on the acceleration of a so-called free piston, whose inertia is used to compress the gas until the membrane ruptures, will be described hereinbelow with reference to FIGS. 8 and 9.

Figure 8:
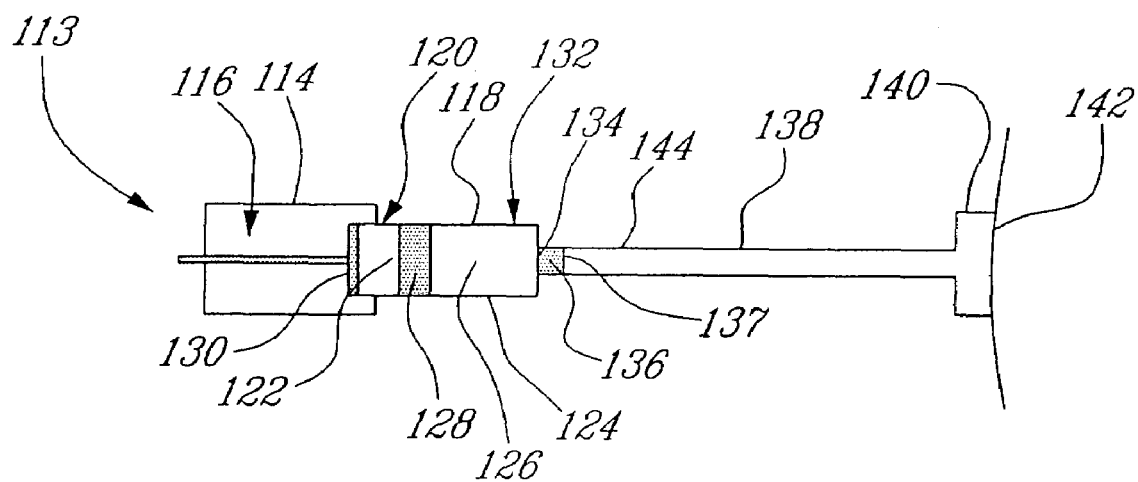

FIG. 8 schematically illustrates the various parts of a gas compression needleless syringe 113 according to a fourth embodiment of the present invention. The triggering assembly of the syringe 113 comprises a reserve 114 filled with compressed air or any other compressed gas 116, that is mounted upstream from a reservoir 118. The reservoir 118 comprises a first chamber 120 that is filled with air or an inert gas 122 at atmospheric pressure and a second chamber 124, filled with an inert gas 126 at atmospheric pressure.

A piston 128 is positioned between the first chamber 120 and the second chamber 124. Additionally, a release valve 130 is positioned between the reserve 114 and the first chamber 120.

The downstream end 132 of the second chamber 124 comprises a membrane 134 against which is placed a particle dose 136. A second membrane 137 encloses the particle dose 136. The needleless syringe 113 additionally comprises a tubular nozzle 138 and a spacer/silencer 140 placed against the target 142.

The advantage of this approach is found in the potential for compressing the inert gas 126 contained in the second chamber 124 of the reservoir 118 to a pressure exceeding that of the compressed air or gas 116 in the reserve 114, by using the inertia of the moving piston 128. Indeed, it has been found that the compressed air or gas 116 in reserve 114, at a pressure of 5 atmospheres for example, is capable of generating a pressure in the second chamber 124 of reservoir 118, reaching about 21 atmospheres. This substantial pressure increase is accompanied by an increase in temperature of a factor of three, which in turn results in a beneficial increase of the speed of sound which thereby amplifies the expansion produced.

The particle dose 136 is positioned in the upstream end 144 of the tubular nozzle 138. The particle dose 136, in another embodiment could potentially also incorporate the upstream membrane 134, the downstream membrane 137, the inert gas 126 at atmospheric pressure, and possibly the tubular nozzle 138. The reserve 114 comprises compressed air or an inert gas 116 at moderate pressures in the order of a few atmospheres, coming from a cylinder or an ampoule.

The syringe 113 is activated by opening the release valve 130, enabling the compressed air or inert gas 116 from the reserve 114 to fill the first chamber 120 and hence accelerate the piston 128 towards the second chamber 124 filled with an inert gas 126. The piston 128 compresses the inert gas 126 to a pressure sufficiently high to rupture the membrane 134, which propels the particle dose 136 toward the target 142.

The inertia of the moving piston 128 is capable of compressing the inert gas 126 to several times the pressure of the compressed air or gas 116, as initially contained in the reserve 114. The spacer/silencer 140 of the syringe 113, can be re-used after sterilization.

Figure 9:
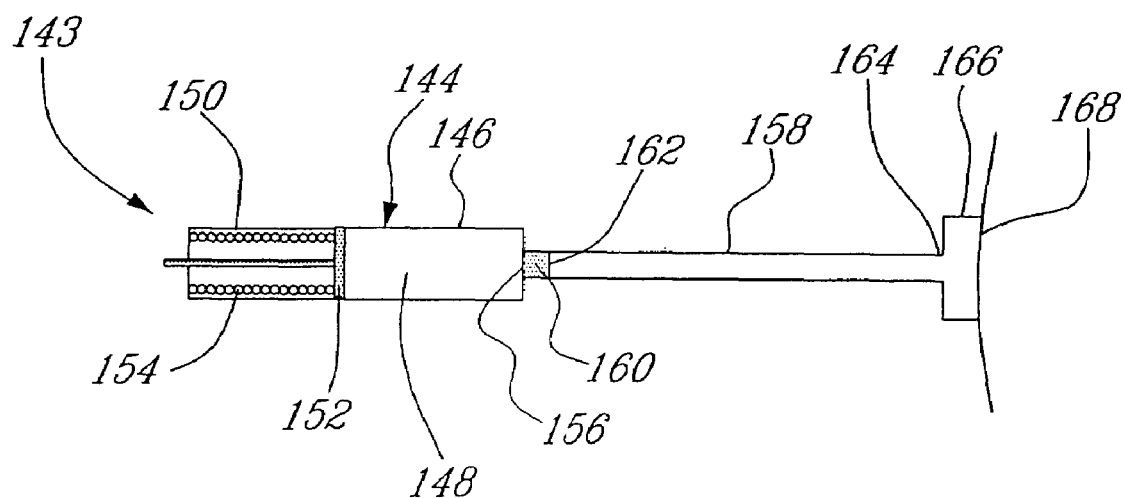

FIG. 9 schematically illustrates the various parts of a gas compression syringe 143 in accordance with a fifth embodiment of the present invention.

This approach eliminates all sources of compressed gas. The triggering assembly of the syringe 143 includes a cylindrical reservoir 144 that comprises a downstream chamber 146, filled with an inert gas 148 at atmospheric pressure or above, and an upstream chamber 150 open to the atmosphere. A piston 152 separates the upstream chamber 150 from the downstream chamber 146. A compression spring 154 (shown in its compressed state) is positioned in the upstream chamber 150 and is connected to the piston 152.

The syringe 143 additionally comprises a tubular nozzle 158 mounted to the downstream end of the cylindrical reservoir 144. A particle dose 160, comprising an upstream membrane 156 and a downstream membrane 162, is positioned at the upstream end of the tubular nozzle 158. The tubular nozzle 158 is in contact with the chamber 146.

The exit 164 of the tubular nozzle 158 is mounted to a spacer/silencer 166, which is placed against the target 168.

In another embodiment, the particle dose 160 could potentially also incorporate the membranes 156 and 162, the inert gas 148, either at atmospheric pressure or above, and possibly the tubular nozzle 158.

To activate the syringe 143, the piston 152 is freed which allows the spring 154 to propel the piston 152 in the downstream direction resulting in the compression of the inert gas 148 contained in the downstream chamber 146 of the reservoir 144. The piston 152 compresses the inert gas 148 to a pressure sufficiently high to rupture the membranes 156 and 162 propelling the particle dose 160 towards the target 168. Again, using the mass of the piston 152, the potential energy of the spring is capable of pushing the piston towards the inert gas, resulting in the compression of the inert gas to several times the quasi-static pressure achievable by the steady-state extension of the spring. The spacer/silencer 166 can be re-used after sterilization.

Of course, means must be provided to retain the piston in its position shown in FIG. 8 and to compress it so that this position may be achieved.

It is conceivable that the needleless syringes of the present invention, taking advantage of mechanisms for the direct compression of an inert gas, could be composed of disposable parts such as for example a module comprising the tubular nozzle, the particle dose as well as the inert gas, all contained in a thin and flexible bag at atmospheric or higher pressures. Additionally, these needleless syringes could be composed of re-usable parts such as the housing, as well as the piston and its triggering and accelerating mechanism. The interest of using these kinds of needleless syringes is essentially found in the sterility that they provide, since the exposed parts would be disposed of after each application.

It is obvious that while using the needleless syringe of the present invention, the propagation of micro-organisms from one patient to another has to be avoided. The replacement of all the components that either could or are in contact with the patient, such as for example the spacer/silencer, the tubular nozzle and the reservoir, should therefore be replaced. It is therefore advantageous that the primary configuration allows for a rapid disassembly of the syringe between each use, such that the above-mentioned components can be replaced. It is apparent that several of the above-mentioned proposed improvements, strongly encourage the sterility aspect and ease of operation of the needleless syringe.

The present invention allows for a more efficient and more predictable acceleration of therapeutic agents, as compared with the needleless syringes described in the prior art. Essentially, the needleless syringe of the present invention, produces an acceleration of the therapeutic agents, that is principally induced by a combination of non-stationary and steady expansion waves, in a uni-dimensional nozzle. Additionally, the needleless syringe of the present invention prevents the separation of the particle flow by using an elongate tubular nozzle of constant cross section.

The terms and descriptions used herein are preferred embodiments set forth by way of illustration only, and are not intended as limitations on the many variations which those of skill in the art will recognize to be possible in practicing the present invention. It is the intention that all possible variants whether presently known or unknown, that do not have a material effect upon the way the invention works, are to be covered by the appended claims. Accordingly, those specialized in the area covered by the present invention will certainly be in a position to apply modifications or adaptations to the details described in the preferred embodiment, while being constrained within the framework of the appended claims.

What is claimed is:

1. A needleless syringe for delivering therapeutic particles to a skin surface, comprising:

a gas reservoir for receiving a gas at a first pressure, the gas reservoir having a first internal diameter and an opening;

an elongate tubular nozzle having an upstream end mounted to the opening of the gas reservoir, an upstream portion and a downstream end;

an arrangement comprising:

the elongate tubular nozzle having a generally constant second internal diameter smaller than the first internal diameter and being at a second internal a pressure;

a contraction of the gas reservoir from the first internal diameter to the second internal diameter;

a source of therapeutic particles positioned in the upstream end of the elongated tubular nozzle of generally constant second internal diameter; and a partition for separating the gas reservoir from the source of particles, the partition being designed to be opened and to withstand large pressure differences between the gas reservoir and the elongate tubular nozzle; and wherein the first and second internal diameters and the first and second gas pressures define respective, predetermined diameter and pressure ratios adapted to produce, in response to opening of the partition, a gaseous expansion generating a) a stationary expansion wave in the contraction leading to a sonic flow at the upstream end of the tubular nozzle and b) non-stationary expansion waves traveling downstream in the elongate tubular nozzle to carry the therapeutic particles into a supersonic gas flow and deliver the therapeutic particles to the skin surface through the downstream end of the tubular nozzle.

2. A needleless syringe as recited in claim 1, wherein said opening of said partition further generates an unsteady expansion traveling upstream into said reservoir.

3. A needleless syringe as recited in claim 2, wherein said opening of said partition further generates a shock wave in said elongate tubular nozzle.

4. A needleless syringe as recited in claim 1, wherein said reservoir is pre-loaded with pressurized gas.

5. A needleless syringe as recited in claim 1, wherein a pattern of stationary and non-stationary expansion waves is generated at said downstream end of said elongate tubular nozzle when said gaseous expansion and said particles reach the exit of said elongate tubular nozzle.

6. A needleless syringe as recited in claim 1, wherein the particles exit said downstream end of said tubular nozzle with respective velocities having an essentially spatially uniform and parallel distribution.

7. A needleless syringe as recited in claim 1, further comprising i) a gas reserve mounted at an upstream end of said gas reservoir and containing a source of pressurized gas, and ii) a release valve separating said pressurized gas source from said gas reservoir, said gas reservoir being at essentially atmospheric pressure; whereby the opening of said release valve allows the pressurized gas to fill said gas reservoir until said partition ruptures generating a) said stationary expansion wave in said contraction leading to the sonic flow at the upstream end of the tubular nozzle and b) said non-stationary expansion waves traveling downstream in said elongate tubular nozzle, accelerating the particles towards said downstream end of said tubular nozzle.

8. A needleless syringe as recited in claim 7, wherein said release valve includes a small diameter orifice controlling the flow rate of said pressurized gas into said reservoir upon opening of said release valve.

9. A needleless syringe as recited in claim 8, wherein said downstream end of said tubular nozzle is enlarged to form a spacer between said downstream end and a target plane, said spacer being so shaped as to create a substantially normal wave near the surface of the target plane.

10. A needleless syringe as recited in claim 9, wherein said substantially normal wave decelerates the particles, generating a radially uniform particle velocity distribution.

11. A needleless syringe as recited in claim 1, further comprising a silencer mounted to the downstream end of said tubular nozzle.

12. A needleless syringe as recited in claim 1, wherein said gas reservoir further comprises:

a compressed gas reserve;

a first chamber filled with a gas substantially at atmospheric pressure and a second chamber filled with a gas at atmospheric pressure;

a piston separating said first chamber from said second chamber;

a release valve separating said compressed gas reserve from said first chamber;

a membrane forming said partition and separating the gas of said second chamber from said tubular nozzle;

whereby opening said release valve allows the compressed gas from the reserve to fill said first chamber pushing said piston into said second chamber, compressing the gas into said second chamber until said membrane ruptures, generating a) said stationary expansion wave in said contraction leading to the sonic flow at the upstream end of the tubular nozzle and b) said non-stationary expansion waves traveling downstream in said elongate tubular nozzle, accelerating the particles towards said downstream end of said nozzle.

13. A needleless syringe as recited in claim 12, wherein said piston has an inertia capable of compressing said compressed gas reserve to several times the pressure of said compressed gas.

14. A needleless syringe as recited in claim 1, wherein said reservoir further comprises:

a downstream chamber filled with a gas at substantially atmospheric pressure and an upstream chamber;

a piston attached to a compressed spring and separating said upstream chamber and said downstream chamber;

a membrane forming said partition and separating the gas of said upstream chamber from said tubular nozzle;

whereby releasing said compressed spring pushes said piston into said upstream chamber thereby compressing the gas in said upstream chamber causing said membrane to rupture, generating a) said stationary expansion wave in said contraction leading to the sonic flow at the upstream end of the tubular nozzle and b) said non-stationary expansion waves traveling downstream in said elongate tubular nozzle, accelerating the particles towards said downstream end of said nozzle.

15. A needleless syringe as recited in claim 14, wherein said piston has an inertia capable of compressing said compressed gas reserve to several times the pressure of said compressed gas.

16. A needleless syringe as defined in claim 1, wherein the second internal pressure of the elongate tubular nozzle is initially lower than the atmospheric pressure.

17. A needleless syringe as defined in claim 1, wherein the ratio of the first internal diameter to the second internal diameter is about 3.2.

18. A needleless syringe as defined in claim 1, wherein the ratio of the first internal diameter to the second internal diameter is about 3.75.

19. A needleless syringe as defined in claim 1, wherein the ratio of the first internal diameter to the second internal diameter is equal to or larger than 3.2.

20. A needleless syringe as defined in claim 1, wherein the gas received in the gas reservoir is an inert gas and wherein the ratio of the first gas pressure to the second gas pressure is situated between about 20 and about 80.

21. A needleless syringe as defined in claim 20, wherein the inert gas comprises helium.

22. A needleless syringe as defined in claim 1, wherein the ratio of the first internal diameter to the second internal diameter is equal to or larger than 3.2, wherein the gas received in the gas reservoir is an inert gas and wherein the ratio of the first gas pressure to the second gas pressure is situated between about 20 and about 80.

23. A needleless syringe as defined in claim 1, wherein the second internal diameter of the tubular nozzle is 4 mm.

24. A needleless syringe as defined in claim 1, wherein the second internal diameter of the tubular nozzle is 4.9 mm.

25. A needleless syringe as defined in claim 1, wherein the second internal diameter of the tubular nozzle is equal to or larger than 4 mm.

26. A needleless syringe as defined in claim 1, wherein the tubular nozzle has a length and wherein a ratio of the length of the tubular nozzle to the constant second internal diameter of the nozzle is 12.5.

27. A method for delivering therapeutic particles to a skin surface, comprising:

providing a gas reservoir for receiving a gas at a first pressure, the gas reservoir having a first internal diameter and an opening;

mounting an upstream end of an elongate tubular nozzle to the opening of the gas reservoir, the elongate tubular nozzle also comprising an upstream portion and a downstream end;

forming the elongate tubular nozzle with a generally constant second internal diameter smaller than the first internal diameter, the elongate tubular nozzle being at a second internal gas pressure;

contracting the gas reservoir from the first internal diameter to the second internal diameter;

placing a source of therapeutic particles in the upstream end of the elongated tubular nozzle having a generally constant second internal diameter;

separating the gas reservoir from the source of particles by means of a partition designed to be opened and to withstand large pressure differences between the gas reservoir and the elongate tubular nozzle; and providing a predetermined diameter ratio of the first internal diameter to the second internal diameter and a predetermined pressure ratio of the first gas pressure to the second gas pressure to produce, in response to opening of the partition, a gaseous expansion generating a) a stationary expansion wave in the contraction leading to a sonic flow at the upstream end of the tubular nozzle and b) non-stationary expansion waves traveling downstream in the elongate tubular nozzle to carry the therapeutic particles into a supersonic gas flow and deliver the therapeutic particles to the skin surface through the downstream end of the tubular nozzle.

28. A method as recited in claim 27, further including:

providing a gas reserve containing a source of pressurized gas, the gas reservoir being at substantially atmospheric pressure; and providing a release valve, wherein said gas reserve is mounted to an upstream end of said gas reservoir and wherein said release valve separates said pressurized gas from said gas reservoir;

wherein generating a) said stationary expansion wave in said contraction leading to a sonic flow at the upstream end of the tubular nozzle and b) said non-stationary expansion waves traveling downstream in said elongate tubular nozzle comprises opening the release valve to allow the pressurized gas to fill the gas reservoir until the partition opens to thereby accelerate the particles towards the downstream end of the nozzle.

29. A method as recited in claim 27, comprising producing, at the downstream end of the tubular nozzle, an essentially spatially uniform and parallel particle velocity distribution.

30. A method as recited in claim 27, wherein the opening of the partition produces an unsteady expansion traveling upstream into said gas reservoir, and wherein said unsteady expansion travels in a downstream direction after reflecting from an upstream end of the gas reservoir.

31. A method as recited in claim 30, comprising producing an essentially constant high velocity flow that terminates when the leading front of said reflected unsteady expansion reaches the downstream end of the nozzle.

32. A method as recited in claim 27, comprising controlling the velocity of the particles impacting a target surface by selecting a) initial and physical properties of the gases comprised in the gas reservoir and said nozzle and b) the ratio of said first internal diameter to said second internal diameter and c) the ratio of the first gas pressure to the second gas pressure.

33. A method as recited in claim 27 wherein providing a gas reservoir includes:

providing a first chamber filled with a first pressurized gas;

providing a second chamber downstream from the first chamber and including a closed orifice that may be opened to the atmosphere, the second chamber being filled with a second gas at a lower pressure relative to the first gas;

providing a first membrane separating the first chamber from the second chamber;

providing a second membrane separating the second chamber from the tubular nozzle;

wherein producing non-stationary expansion waves comprises opening the orifice to cause a pressure-drop in the second chamber resulting in the rupturing of said first membrane whereby the first pressurized gas fills the second chamber in turn rupturing said second membrane, generating a) said stationary expansion wave in said contraction leading to the sonic flow at the upstream end of the tubular nozzle and b) said non-stationary expansion waves traveling downstream in said elongate tubular nozzle, accelerating the particles towards the downstream end of the nozzle.

34. A method as recited in claim 27, wherein providing a gas reservoir includes:

providing a compressed gas reserve;

providing a first chamber filled with a gas at atmospheric pressure and a second chamber filled with a gas at atmospheric pressure;

providing a piston separating the first chamber from the second chamber;

providing a release valve separating the compressed gas reserve from the first chamber;

providing a membrane forming the partition and separating the gas of the second chamber from the tubular nozzle;

wherein generating a) said stationary expansion wave in said contraction leading to a sonic flow at the upstream end of the tubular nozzle and b) said non-stationary expansion waves traveling downstream in said elongate tubular nozzle comprises opening the release valve to allow the compressed gas to fill the first chamber pushing the piston into the second chamber, compressing the gas in the second chamber until the membrane ruptures, generating a) said stationary expansion wave in said contraction leading to the sonic flow at the upstream end of the tubular nozzle and b) said non-stationary expansion waves traveling downstream in said elongate tubular nozzle, accelerating the particles towards the downstream end of the nozzle.

35. A method as recited in claim 34, further comprising compressing said compressed gas reserve to several times the pressure of said compressed gas by means of the inertia of said piston.

36. A method as recited in claim 27, wherein providing a gas reservoir includes:

providing a downstream chamber filled with a gas at substantially atmospheric pressure and an upstream chamber;

providing a piston attached to a compressed spring and separating the upstream chamber and the downstream chamber; and providing a membrane forming a partition and separating the gas of the downstream chamber from the tubular nozzle;

wherein generating a) said stationary expansion wave in said contraction leading to a sonic flow at the upstream end of the tubular nozzle and b) said non-stationary expansion waves traveling downstream in said elongate tubular nozzle comprises releasing the compressed spring to push the piston into the downstream chamber thereby compressing the gas in the downstream chamber causing the membrane to rupture, generating a) said stationary expansion wave in said contraction leading to the sonic flow at the upstream end of the tubular nozzle and b) said non-stationary expansion waves traveling downstream in said elongate tubular nozzle, accelerating the particles towards the downstream end of the nozzle.

37. A method as recited in claim 36, further comprising compressing said compressed gas reserve to several times the pressure of said compressed gas by means of the inertia of said piston.

38. A method for delivering therapeutic particles as defined in claim 27, wherein the second internal gas pressure of the elongate tubular nozzle is initially lower than atmospheric pressure.

39. A method for delivering therapeutic particles as defined in claim 27, wherein the ratio of the first internal diameter to the second internal diameter is about 3.2.

40. A method for delivering therapeutic particles as defined in claim 27, wherein the ratio of the first internal diameter to the second internal diameter is about 3.75.

41. A method for delivering therapeutic particles as defined in claim 27, wherein the ratio of the first internal diameter to the second internal diameter is equal to or larger than 3.2.

42. A method for delivering therapeutic particles as defined in claim 27, wherein the gas received in the gas reservoir is an inert gas and wherein the ratio of the first gas pressure to the second gas pressure is situated between about 20 and about 80.

43. A method for delivering therapeutic particles as defined in claim 42, wherein the inert gas comprises helium.

44. A method for delivering therapeutic particles as defined in claim 27, wherein the ratio of the first internal diameter to the second internal diameter is equal to or larger than 3.2, wherein the gas received in the gas reservoir is an inert gas and wherein the ratio of the first gas pressure to the second gas pressure is situated between about 20 and about 80.

45. A method for delivering therapeutic particles as defined in claim 27, wherein the second internal diameter of the tubular nozzle is 4 mm.

46. A method for delivering therapeutic particles as defined in claim 27, wherein the second internal diameter of the tubular nozzle is 4.9 mm.

47. A method for delivering therapeutic particles as defined in claim 27, wherein the second internal diameter of the tubular nozzle is equal to or larger than 4 mm.

48. A method for delivering therapeutic particles as defined in claim 27, wherein the tubular nozzle has a length and wherein a ratio of the length of the tubular nozzle to the constant second internal diameter of the nozzle is 12.5.

49. A needleless syringe, for delivering therapeutic particles to a skin surface, comprising:
a gas reservoir having a first internal diameter and an opening;
an elongate tubular nozzle having an upstream end mounted to the opening of the gas reservoir and a downstream end;
an arrangement for producing non-stationary expansion waves traveling downstream in the elongate tubular nozzle and for carrying by means of the non-stationary expansion waves the therapeutic particles at a velocity sufficient to deliver the therapeutic particles to the skin surface, the arrangement comprising:
the elongate tubular nozzle having a generally constant second internal diameter;
a contraction of the gas reservoir from the first diameter to the second diameter;
an upstream portion of the elongated tubular nozzle of generally constant second internal diameter for accommodating a source of therapeutic particles;
a rupturable partition for separating the gas reservoir from the source of particles, the partition being designed to withstand large pressure differences between the gas reservoir and the elongate tubular nozzle; and
a ratio of the first internal diameter to the second internal diameter which is sufficient to allow the contraction of the gas reservoir to produce, in response to a rupture of the partition caused by a difference of gas pressure between the gas reservoir and the elongate tubular nozzle, a gaseous expansion generating a) a stationary expansion wave in the contraction leading to a sonic flow at the upstream end of the tubular nozzle and b) the non-stationary expansion waves traveling downstream in the elongate tubular nozzle to carry the therapeutic particles into a supersonic gas flow;
wherein said gas reservoir further comprises:
a first chamber filled with a first pressurized gas;
a second chamber mounted downstream from said first chamber and including a closed orifice that may be opened to the atmosphere, said second chamber being filled with a second gas at a lower pressure relative to the first gas;
a first membrane separating said first chamber from said second chamber; a second membrane separating said second chamber from said tubular nozzle;
whereby opening said orifice to the atmosphere results in a pressure-drop in said second chamber resulting in a rupture of said first membrane whereby the first pressurized gas fills the second chamber in turn rupturing said second membrane, generating a) said stationary expansion wave in said contraction leading to a sonic flow at the upstream end of the tubular nozzle and b) said non-stationary expansion waves traveling downstream in said elongate tubular nozzle, accelerating the particles into a supersonic gas flow towards said downstream and of said nozzle.

50. A needleless syringe for delivering particles, said syringe comprising:
a first reservoir having a first internal diameter, said reservoir having an opening defining a contraction;
an elongate tubular nozzle having an upstream end and a downstream end; said elongate tubular nozzle having a generally constant second internal diameter;
a second reservoir interposed between the opening of said first reservoir and said tubular nozzle, said second reservoir having substantially said second internal diameter;
a first partition separating said first reservoir from said second reservoir;
a second partition separating said second reservoir from said tubular nozzle;
whereby positively pressurizing with a gas said first reservoir relative to said second reservoir results in rupturing said first partition whereby said gas fills the second reservoir in turn rupturing said second partition, generating a) a stationary expansion wave in said contraction leading to a sonic flow at the upstream end of the tubular nozzle and b) non-stationary expansion waves traveling downstream in said elongate tubular nozzle, accelerating the particles into a supersonic gas flow towards said downstream end of said nozzle;

wherein said first reservoir is filled with a positively pressurized gas relative to the atmospheric pressure, and wherein said second reservoir further comprises a closed orifice that may be opened to the atmosphere for causing said positive pressurizing of said first reservoir relative to said second reservoir.

51. A method for delivering particles comprising:

providing a first reservoir having a first internal diameter; the reservoir having an opening defining a contraction;

providing an elongate tubular nozzle having an upstream end and a downstream end; the elongate tubular nozzle having a generally constant second internal diameter;

interposing a second reservoir between the opening of said first reservoir and said tubular nozzle, said second reservoir having substantially said second internal diameter;

separating said first reservoir from said second reservoir with a first partition;

separating said second reservoir from said tubular nozzle with a second partition; and positively pressurizing with a gas said first reservoir relative to said second reservoir to rupture said first partition whereby said gas fills the second reservoir in turn rupturing said second partition, generating a) a stationary expansion wave in said contraction leading to a sonic flow at the upstream end of the tubular nozzle and b) non-stationary expansion waves traveling downstream in said elongate tubular nozzle, accelerating the particles into a supersonic gas flow towards said downstream end of said nozzle;

wherein said method further comprises filling said first reservoir with a positively pressurized gas relative to the atmospheric pressure, and providing in said second reservoir a closed orifice and opening said orifice to the atmosphere for causing said positive pressurizing of said first reservoir relative to said second reservoir.

* * * * *